US009636385B2

(12) United States Patent
Honkanen

(10) Patent No.: US 9,636,385 B2
(45) Date of Patent: May 2, 2017

(54) USE OF COLLAGENASE TO TREAT GLAUCOMA

(71) Applicant: The Research Foundation for The State University of New York, Albany, NY (US)

(72) Inventor: Robert Honkanen, Sound Beach, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/438,385

(22) PCT Filed: Oct. 24, 2013

(86) PCT No.: PCT/US2013/066589
§ 371 (c)(1),
(2) Date: Apr. 24, 2015

(87) PCT Pub. No.: WO2014/066622
PCT Pub. Date: May 1, 2014

(65) Prior Publication Data
US 2015/0273028 A1    Oct. 1, 2015

Related U.S. Application Data

(60) Provisional application No. 61/717,837, filed on Oct. 24, 2012.

(51) Int. Cl.
| | | |
|---|---|---|
| *A61K 38/46* | (2006.01) | |
| *A61K 38/48* | (2006.01) | |
| *A61K 9/00* | (2006.01) | |
| *A61K 47/22* | (2006.01) | |
| *A61F 9/007* | (2006.01) | |

(52) U.S. Cl.
CPC ........ *A61K 38/4886* (2013.01); *A61K 9/0048* (2013.01); *A61K 47/22* (2013.01); *C12Y 304/24003* (2013.01); *A61F 9/00781* (2013.01)

(58) Field of Classification Search
None
See application file for complete search history.

(56) References Cited

U.S. PATENT DOCUMENTS

| | | |
|---|---|---|
| 3,267,006 A | 8/1966 | Hakim et al. |
| 3,705,083 A | 12/1972 | Chiulli et al. |
| 3,821,364 A * | 6/1974 | Chiulli et al. ........... C12N 9/52 424/94.63 |
| 4,174,389 A | 11/1979 | Cope |
| 4,338,300 A | 7/1982 | Gelbard |
| 4,524,065 A | 6/1985 | Pinnell |
| 4,645,668 A | 2/1987 | Pinnell |
| 5,173,295 A | 12/1992 | Wehling |
| 5,279,825 A | 1/1994 | Wehling |
| 5,332,503 A | 7/1994 | Lee et al. |
| 5,393,792 A | 2/1995 | Stern et al. |
| 5,422,103 A | 6/1995 | Stern et al. |
| 5,514,370 A | 5/1996 | Stern et al. |
| 5,589,171 A | 12/1996 | Wegman |
| 5,753,485 A | 5/1998 | Dwulet et al. |
| 5,830,741 A | 11/1998 | Dwulet et al. |
| 5,952,215 A | 9/1999 | Dwulet et al. |
| 5,989,888 A | 11/1999 | Dwulet et al. |
| 6,022,639 A | 2/2000 | Urry |
| 6,060,474 A | 5/2000 | Williams et al. |
| 6,086,872 A | 7/2000 | Wegman |
| 6,086,877 A | 7/2000 | Nishioka et al. |
| 6,280,993 B1 | 8/2001 | Yamato et al. |
| 6,335,388 B1 | 1/2002 | Fotinos |
| 6,358,539 B1 | 3/2002 | Murad |
| 6,958,150 B2 | 10/2005 | Wegman et al. |
| RE39,941 E | 12/2007 | Wegman |
| 7,425,326 B2 | 9/2008 | Strauss |
| 7,854,929 B2 | 12/2010 | Badalamente et al. |
| 2003/0129178 A1 | 7/2003 | Wegman et al. |
| 2004/0137596 A1 | 7/2004 | Kurfurst et al. |
| 2006/0122152 A1* | 6/2006 | Peyman ............ A61K 31/65 514/56 |
| 2006/0204488 A1 | 9/2006 | Badalamente |
| 2007/0224183 A1 | 9/2007 | Sabatino et al. |
| 2007/0224184 A1 | 9/2007 | Badalamente et al. |
| 2010/0247513 A1 | 9/2010 | Agee et al. |

FOREIGN PATENT DOCUMENTS

| | | |
|---|---|---|
| EP | 0677586 | 10/1995 |
| EP | 1433845 | 6/2004 |
| JP | 2003523319 | 8/2003 |
| WO | WO 01/21574 | 3/2001 |
| WO | WO 2007/089851 | 8/2007 |

OTHER PUBLICATIONS

Jiang et al. Pharm Res. Feb. 2009 ; 26(2): 395-403.*
Whitson et al. Journal of Ocular Pharmacology and Therapeutics, vol. 26, No. 3, 2010, pp. 287-292.*
Sawyer, Jeffrey R. et al., A reciprocal t(4;9)(q31;p22) in a solitary neurofibroma, Cancer Genetics and Cytogenetics 156 (2005) 172-174, Copyright 2005 Elsevier Inc.
Auxilium Pharmaceuticals Inc. (AUXL) DEF 14A Definitive proxy statements, Filed on Apr. 27, 2012, Filed Period Jun. 21, 2012, Thomson Reuters Accelus, pp. 90.
Angehrn, Fiorenzo et al., Can cellulite be treated with low-energy . . . , Clinical Investigations in Aging 2007:2(4) 623-630, Copyright 2007 Dove Medical Press Limited.
Welton, RL et al., Collagenase production by Achromobacter iophagus, Biochim Biophys Acta. Mar. 28, 1975;384(1):228-34, Abstract.

(Continued)

*Primary Examiner* — Chris R Tate
*Assistant Examiner* — Douglas F White
(74) *Attorney, Agent, or Firm* — The Farrell Law Firm, P.C.; John F. Gallagher, III

(57) ABSTRACT

Provided is a method of treatment for reducing fibrosis involving administering purified collagenase into an anterior chamber of an eye of a human patient.

5 Claims, No Drawings

(56) References Cited

OTHER PUBLICATIONS

Badalamente, Marie A. et al., Enzymatic Capsulotomy for Adhesive Capsulitis (Frozen Shoulder) . . . , 61st Annual Am. Society for Surgery of the Hand, Sep. 2006, pp. 2.
Hannafin, Jo A. et al., Adhesive Capsulitis a Treatment Approach, Clinical Orthopaedics and Related Research, No. 372, 2000, pp. 95-109.
Siegel, Lori B. et al., Adhesive Capsulitis: A Sticky Issue, American Family Physician, The American Academy of Family Physicians, Apr. 1, 1999, pp. 12.
Hulstyn, Michael J. et al., Adhesive Capsulitis of the Shoulder, Orthopaedic Review, Apr. 1993, pp. 425-433.
Bond, Michael D., et al., Characterization of the Individual Collagenases from Clostridium histolyticum, Biochemistry, vol. 23, No. 13, 1984, pp. 3085-3091.
Hosaka, T. et al., Class2 collagenase, GenBank: BAA86030.1, http://www.ncbi.nlm.nih.gov/protein/BAA86030.1, Published Only in Database (1999), Submitted (Apr. 30, 1999), pp. 2.
Chen, Hong-Rong et al., Clinicopathological Study on Submucosal Injection of Collagenase in the Treatment of Submucous Fibrosis . . . , Kaohsiung J. Med. Sci. 2: 212-219, 1986.
Badalamente, Marie A. et al., Collagen as a Clinical Target: Nonoperative Treatment of Dupuytren's . . . , The Journal of Hand Surgery, vol. 27A No. 5, Sep. 2002, pp. 788-798.
Worthington Enzyme Manual, Copyright 2012—Worthington Biochemical Corporation, pp. 4.
Kilian, O. et al., The frozen shoulder. Athroscopy, histological findings and transmission electron microscopy imaging, Chirurg, 2001, 72, pp. 1303-1308.
De-Wever, Ivo et al., Cytogenetic, Clinical, and Morphologic Correlations . . . , Copyright 2000 The U.S. and Canadian Academy of Pathology, Inc., vol. 13, No. 10, pp. 1080-1085.
Hutchinson, J. W. et al., Dupuytren's disease and frozen shoulder induced . . . , The Journal of Bone & Joint Surgery (Br), vol. 80-B, No. 5, Sep. 1998, pp. 907-908.
Badalamente, Marie A. et al., Efficacy and Safety of Injectable Mixed Collagenase Subtypes in . . . , The Journal of Hand Surgery, vol. 32A No. 6 Jul.-Aug. 2007, pp. 767-774.
Badalamente M.A. et al: "Enzyme injection as a nonoperative treatment for Dupuytren's disease", Drug Delivery, vol. 3, 1996, pp. 35-40, XP000993396.
Ippolito, E. et al., Experimental study on the use of collagenase in localized connective tissue . . . , Ital. J. Orthop. Traumatol., (1975) vol. 1, No. 2, pp. 279-290, Abstract.
Bunker, T. D., Frozen shoulder: unravelling the enigma, Ann R Coll Surg Engl 1997; 79, pp. 210-213.
Yamato, I., et al., Gene encoding class I collagenase, GenBank: AAE80094.1, http://www.ncbi.nlm.nih.gov/protein/AAE80094, U.S. Pat. No. 6,280,993-A 3 Aug. 28, 2001, pp. 2.
WebMD Health News, Goodbye, Cellulite Thighs?, Copyright 2005-2007 WebMD, Inc., pp. 2.
Jung, Chang-Min et al., Identification of Metal . . . , Journal of Bacteriology, vol. 181, No. 9, May 1999, p. 2816-2822, Copyright 1999, American Society for Microbiology.
Oppenheim, F. et al., A modified procedure for the purification of clostridial collagenase, Prep Biochem. 1978;8(5):387-407, Abstract.
Galardy, Richard E. et al., Inhibition of Collagenase from Clostridium histolyticum by Phosphoric and Phosphonic Amides, Biochemistry, vol. 22, No. 19, 1983, pp. 4456-4561.
Hurst, Lawrence C. et al., Injectable Clostridial Collagenase: Striving Toward Non . . . , (2009) http://www.aos.org/research/committee/research/KAPPA/KD2009_Hurst.pdf.
Rotunda, Adam M. et al., Mesotherapy and Phosphatidylcholine Injections: Historical . . . , Copyright 2006 by the American Society for Dermatologic Surgery, Inc., pp. 465-480.
Dimarcantonio, Tina, Multiple collagenase injections effective, safe for treating 'frozen shoulder', www.ORTHOSuperSite.com, May 16, 2006, pp. 2.
Mandl, Ines et al., Multiplicity of Clostridium histolyticum Collagenases, Multiplicity of Collagenases, vol. 3, No. 11, Nov. 1964, pp. 1737-1741.
Ochs, Ridgely, Personal Health/Promising New Treatments for Stiff-Shoulder Condition, www.Newsday.com, Oct. 1, 2001, pp. 3.
Bains, M. et al., Journal of Bone and Joint Surgery, Primary Frozen Shoulder, The Untold Story!, British Volume, vol. 90-B, Issue SUPP_II, 352, (Abstract) 2008, pp. 2.
Park, Pyo-Jam et al., Purification and Characterization of a Collagenase from the . . . , Journal of Biochemistry and Molecular Biology, vol. 35, No. 6, Nov. 2002, pp. 576-582.
Sugasawara, R. et al., Purification and characterization of three forms of collagenase from Clostridium histolyticum, Biochemistry Oct. 23, 1984;23(22):5175-81, Abstract.
Nagano, Hiroko et al., Purification of Collagenase and Specificity of Its Related Enzyme from Bacillus subtilis FS-2, Biosci. Biotechnol. Biochem., 63 (7) 1999, pp. 181-183.
Ambrosius, D.D. et al., Recombinant collagenase type II from clostridium . . . , GenBank:CAA02888.1, http://www.ncbi.nlm.nih.gov/proteinCAA02888, Patent: EP0677586-A1, Oct. 18, 1995.
Jin, Bo et al., Reversibility of experimental rabbit liver cirrhosis by portal collagenase administration, Laboratory Investigation (2005) 85, 992-1002, 2005 USCAP, Inc.
Netti, Paolo A. et al., Role of Extracellular Matrix . . . , ICancer Research 60. 2497-2503. May I. 20001, Copyright 2000 American Association for Cancer Research, pp. 2497-2503.
Balci, N. et al., Shoulder adhesive capsulitis and shoulder range of motion in type II diabetes mellitus . . . , Journal of Diabetes, May-Jun. 1999(3): 135-40 (Abstract).
Keil, B., Some newly characterized collagenases from procaryotes and lower eucaryotes, Mol Cell Biochem. Jan. 26, 1979;23(2) 87-108, Abstract.
Griffith, James F. et al., Sonography of Plantar Fibromatosis, AJR:179, Nov. 2002, pp. 1167-1172.
Stony Brook Announces New Clinical Trial with BioSpecifics' Injectable Collagenase for Adhesive Capsulitis, http://web.archive.org/web/20011020004505/, May 8, 2012, (pp. 2).
Matsushita, Osamu et al., Substrate Recognition by the Collagenbinding Domain . . . , The Journal of Biological Chemistry, vol. 276, No. 12, Issue of Mar. 23, pp. 8761-8700, 2001.
Successful phase II results lead to phase III approval-Dupuytren disease, obgyn.net Headline News, Oct. 8, 2001 (Oct. 8, 2001), XP008125855.
Evans, Christopher H., The lanthanide-enhanced affinity chromatography of clostridial collagenase, Biochem. J. (1985) 225, 553-556.
Bunker, T. D. et al, The Pathology of Frozen Shoulder a Dupuytren-Like Disease, The Journal of Bone and Joint Surgery, vol. 77-B, No. 5, Sep. 1995, pp. 677-683.
Gaughan, Earl M. et al., Effects of sodium hyaluronate on tendon healing and adhesion formation in horses, Am J Vet Res, vol. 52, No. 6, May 1991, pp. 764-773.

\* cited by examiner

USE OF COLLAGENASE TO TREAT GLAUCOMA

PRIORITY

This application is a U.S. National Phase entry of PCT/US2013/066589, filed Oct. 24, 2013, and claiming priority to U.S. Provisional Patent Application No. 61/717,837, filed on Oct. 24, 2012, the contents of which are incorporated herein by reference.

BACKGROUND OF THE INVENTION

1. Field of the Invention

The present invention relates generally to a method to reduce or remove fibrosis following glaucoma surgery involving administration of purified collagenase into a patient's eye.

2. Description of the Related Art

Glaucoma is a leading cause of irreversible blindness. About 60.5 million people were affected with glaucoma in 2010, with a predicted increase to approximately 79.6 million by 2020. Approximately fourteen percent of those affected with glaucoma will be bilaterally blinded. Treatments that lower intraocular pressure are common for control of glaucoma, regardless of the type of glaucoma. When medications or lasers cannot effectively control or lower the intraocular pressure to acceptable levels, surgical intervention is often necessary.

Glaucoma filtration surgery, i.e., trabeculectomy, is a commonly performed type of glaucoma surgery. In glaucoma filtration surgery, a small opening, i.e., a fistula, is created between an anterior chamber of an eye and the subconjunctival and sub-Tenon's space of the eye. Aqueous fluid produced by the eye is thereby given an alternative pathway to leave the eye, lowering intraocular pressure.

As a result of glaucoma filtration surgery, however, scarring and fibrosis develops at the subconjunctival and sub-Tenon's tissues. Scarring and fibrosis develops following collagen deposition in the area of the glaucoma filtration surgery. The scarring and fibrosis often results in a gradual reduction of filtration and loss of control of intraocular pressure. Moreover, surgical failures occur in up to 30% of cases. Histologic examination of filtration operations resulting in scarring has shown that obstruction to filtration occurs at the subconjunctival tissues including the Tenons capsule and episcleral tissues. Multiple efforts aimed at improving the healing process have been attempted.

Pharmaceutical agents including steroids, such as Tissue Plasminogen Activator (TPA); Betaaminopropionitrile (BAPN); D-penicillamine; daunorubicin; 5-fluorouracil; and Mitomycin C, have been used in an effort to prevent fibrosis following surgery. However, failures readily occur with such agents.

Mechanical devices, such as metallic shunts and collagen inserts, have also been used to improve healing from glaucoma filtration surgery. Other interventions such as radiation have also been attempted. However, mechanical devices have also been unsuccessful in preventing fibrosis and reduction of filtration.

When glaucoma filtration fails, seton implants are often used to help form a mechanical barrier to prevent formation of scar tissue. However, seton implants are also subject to wound healing after implantation and failure of these devices readily occurs. Failure of seton implants is also due to formation of fibrous scar tissue surrounding the implant, which prevents adequate drainage of aqueous fluid.

SUMMARY OF THE INVENTION

The present invention provides a method for providing collagenase injections to relieve intraocular pressure of patients recovering from glaucoma filtration surgery and implantation of seton implants.

In a preferred embodiment, scarring and fibrous adhesions are dissolved by use of Clostridiopeptidase A derived from bacterium *Clostridium histolyticum*, preferably administered in an absence of triamcinolone or other corticosteroids.

An embodiment provides a method of treatment for reducing fibrosis that includes administering an effective amount of purified collagenase into an anterior segment of an eye, before or after glaucoma surgery, with the anterior segment being a sub-Tenons or episcleral space of the eye, and the purified collagenase is administered alone or in conjunction with fluorescein dye, with the purified collagenase administered in an absence of triamcinolone or other corticosteroids. In an embodiment, the purified collagenase is injected in a dose comprising at least about 15,000 SRC units/mg, applied in one or more injections. In an embodiment, the purified collagenase is injected in a volume of about less than 100 microliters. In an embodiment, the purified collagenase comprises one of collagenase I and collagenase II.

DETAILED DESCRIPTION OF THE PREFERRED EMBODIMENTS

The present invention is related to the discovery of the effectiveness of collagenase injections. That is, the present invention relates to treating a patient by injecting an effective amount of collagenase to affected regions of an eye. The present invention also relates to the use of collagenase in the manufacture of a medicament to treat intraocular scarring and fibrosis occurring after glaucoma filtration surgery and after implantation of seton implants.

As described in U.S. patent application Ser. Nos. 11/335,157 and 11/703,269, published as U.S. Publ. No. 2006-0204488 A1 and 2007-0224184 A1, respectively, collagenase treatment has proven effective for treatment of adhesive capsulitis, also known as frozen shoulder, and for reduction of cellulite. Collagenase injections have been proposed for the treatment of diseases such as Dupuytren's disease, adhesive capsulitis and Peyronie's disease, associated with collagen cords or plaques. See, U.S. Pat. Nos. 5,589,171, 6,086,872, 6,022,539, of Wegman.

The published work of Dr. Badalamente, in Dupuytren's disease forms the rationale for the present invention (Starkweather, K., Lattuga, S., Hurst, L. C., Badalamente, M. A., Guilak, F., Sampson, S. P., Dowd, A., Wisch, D. *Collagenase in the Treatment of Dupuytren's Disease: An in vitro Study*, J. Hand Surg. 21A:490-95, 1996; Badalamente, M. A., Hurst, L. C., *Enzyme Injection as a Non-operative Treatment for Dupuytren's Disease*, J. Drug-Delivery 3(1):35-40, 1996; Hurst, L. C., Badalamente, M. A. (invited authorship) *Non-operative Treatment of Dupuvtren's Disease*, Hand Clinics, G. M. Rayan (Ed.), W. B. Saunders 15(1), 97-107, 1999; Hurst, L. C., Badalamente, M. A. (invited editors & authorship), *Dupuytren's Disease*, R. Tubinana, R. Tubiana, C. Leclercq, L. C. Hurst, M. A. Badalamente (eds), Martin Dunitz Publisher, London (2000); Badalamente, M. A., Hurst, L. C. *Enzyme Injection as a Non-operative Treatment of Dupuytren's Disease*, J. Hands Surg. 25A(4);629-36, 2000; Badalamente, M. A., Hurst, L. C., Hentz, V. R. *Collagen as a Clinical Target: Non-operative Treatment of Dupuytren's Disease*, J. Hand Surg. 27A(5):788-98, 2002, Badalamente, M. A., Hurst, L. C., *Efficacy and Safety of Injectable Mixed Collagenase Subtypes in the Treatment of Dupuvtren's Contracture*, J. Hand. Surg. 32A(6): 767-774, (2007). In Dupuytren's disease, the pathognomonic fibrous cord is often interspersed with a septa-like arrangement of adipose tissue. These present clinically as mattress-type "lumps" of varying sizes, and in Dupuytren's disease, are termed nodules. It has been a consistent clinical fording in both Phase 2 and 3 trials for Dupuytren's disease that after purified Clostridial collagenase injection, not only does the collagenous cord dissolve and rupture when subjected to pressure in extension, but the fibro-fatty nodules also resolve, and harmlessly reabsorb. Therefore, collagenase injected subcutaneously into afflicted areas was postulated to be a safe and effective treatment.

Collagenase is an enzyme that has specific ability to digest collagen. A preferred form of a collagenase is derived from fermentation by *Clostridium histolyticum* and is purified by a chromatographic technique, such as that disclosed in U.S. Pat. No. 7,811,560 to Sabatino. Collagenase naturally produced by *Clostridium histolyticum* once purified will exhibit two distinct peaks when run on an electrophoresis SDS gel. These two distinct peaks are referred to as collagenase I and collagenase II.

One form of purified collagenase used for injection includes two microbial collagenases, referred to as "Collagenase ABC I" and "Collagenase ABC II". Both collagenases are isolated and purified from the fermentation of the bacterium *Clostridium histolyticum* and belong to the same metalloprotease.

Collagenase ABC I is a single polypeptide chain consisting of approximately 1000 amino acids of known sequence. It has an observed molecular weight of 115 kiloDalton (kD), an isoelectric point (pI) between 5.63-5.68, and an extinction coefficient of 1.480. From its activity behavior toward synthetic substrate, it has been determined that Collagenase ABC I is class I *Clostridium histolyticum* collagenase. Collagenase ABC II is also a single polypeptide chain consisting of about 1000 amino acids of deduced sequence. It has an observed molecular weight of 110 kD, an isoelectric point between 5.46-5.57 and an extinction coefficient of 1.576. Collagenase ABC II functionally belongs to the class II *Clostridium histolyticum* collagenase.

The drug substance may have a one to one mass ratio for collagenase ABC I and ABC II with an extinction coefficient of 1.528. Both collagenases require tightly bound zinc and loosely bound calcium for their activity. Collagenase ABC I and Collagenase ABC II are not immunologically crossreactive and have a very broad hydrolyzing reactivity toward all types of collagen. Even though each collagenase shows different specificity, together they show synergistic activity toward collagen.

Lyophilized collagen for injection is purified clostridial collagenase prepared as a lyophilized formulation and may contain about 0.1 mg lactose monohydrate USP per 1,000 ABC units of collagenase activity.

A preferred collagenase composition includes a mixture of collagenase I and collagenase II in a mass ratio of about one to one and having specific activity from about 500 SRC units/mg to about 15,000 SRC units/mg, preferably of at least about 700 SRC units/mg, more preferably of at least about 1000 SRC units/mg, more preferably at least about 1500 SRC units/mg. One SRC unit will solubilize rat tail collagen into ninhydrin reaction material equivalent to 1 nanomole of leucine per minute, at 25 degrees C., pH 7.4. Collagenase has been described in ABC units as well, with 10,000 ABC of approximately 0.58 mg. The potency assay of collagenase is based on the digestion of undenatured collagen (from bovine tendon) at pH 7.2 and 37 degrees C. for 20-24 hours. The number of peptide bonds cleaved are measured by reaction with ninhydrin. Amino groups released by a solubilized digestion control are subtracted. One net ABC unit of collagenase will solubilize ninhydrin reactive material equivalent to 1.09 nanomoles of leucine per minute. One SRC unit equals approximately 6.3 ABC units.

Collagenase administration in the present invention is preferably via injection in a pharmaceutically acceptable liquid carrier. Preferably, the carrier does not interact or deactivate the collagenase. Examples are normal saline and aqueous $NaCl/CaCl_2$ buffer containing 0.9% $NaC_1$ and 2 mM $CaCl_2$.

Treatment of scarring and fibrosis occurring after glaucoma filtration surgery and implantation of seton implants using the present invention is a non-surgical procedure in which collagenase injection is directed at an eye of a patient. In an embodiment of the present invention, collagenase is injected into an anterior segment of the eye. The anterior segment of the eye includes one of a sub-Tenons and an episcleral space of the eye. Injection of collagenase into the sub-Tenons and episcleral space of the eye prevents and reverses fibrosis and formation of scar tissue. Removal of fibrotic tissue and scar tissue present in the sub-Tenons and episcleral space of the eye re-opens a fistula created during surgery.

Advantages of the present inventive technology are that it is minimally invasive, does not require any extended rehabilitation and/or surgery and would return patients to normal activities or daily living.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for treating or reducing fibrosis in a subject undergoing glaucoma surgery, the method comprising:
   administering an effective amount of purified collagenase into an anterior segment of an eye by injection to said subject,
   wherein the effective amount of purified collagenase is administered in conjunction with fluorescein dye,
   wherein the effective amount of purified collagenase is administered before the glaucoma surgery, and
   wherein the purified collagenase is injected in a dose of at least about 15,000 SRC units/mg.

2. The method of claim 1, wherein the anterior segment is a sub-Tenons space of the eye.

3. The method of claim 1, wherein the purified collagenase is Clostridiopeptidase A derived from bacterium *Clostridium histolyticum*.

4. The method of claim 1, wherein purified collagenase is administered in an absence of triamcinolone or other corticosteroids.

5. The method of claim 1, wherein the purified collagenase comprises one of collagenase I and collagenase II.

* * * * *